United States Patent
Oehler

(10) Patent No.: US 7,273,250 B2
(45) Date of Patent: Sep. 25, 2007

(54) METHOD FOR INDIVIDUALLY ADAPTING THE SADDLE OF A TWO-WHEEL VEHICLE

(76) Inventor: Claus Oehler, Prinzregentenstr 4, 86150 Augsburg (DE)

( * ) Notice: Subject to any disclaimer, the term of this patent is extended or adjusted under 35 U.S.C. 154(b) by 410 days.

(21) Appl. No.: 10/484,851

(22) PCT Filed: Jun. 22, 2002

(86) PCT No.: PCT/EP02/06910

§ 371 (c)(1),
(2), (4) Date: Feb. 25, 2004

(87) PCT Pub. No.: WO03/011679

PCT Pub. Date: Feb. 13, 2003

(65) Prior Publication Data

US 2004/0232742 A1    Nov. 25, 2004

(30) Foreign Application Priority Data

Jul. 25, 2001    (DE)    ................ 201 12 013 U

(51) Int. Cl.
*B62J 1/00*    (2006.01)

(52) U.S. Cl. .............. 297/195.1; 297/202; 297/452.28; 702/139

(58) Field of Classification Search ............. 297/195.1, 297/452.28, 202; 29/407.08, 705; 73/862.541, 73/862.637; 425/169; 264/40.4; 702/127, 702/138, 139
See application file for complete search history.

(56) References Cited

U.S. PATENT DOCUMENTS

| | | | |
|---|---|---|---|
| 3,081,129 A * | 3/1963 | Ridder ................ 297/452.28 |
| 4,763,952 A * | 8/1988 | Gaudreau, Jr. ............. 297/383 |
| 4,836,033 A | 6/1989 | Seitz |
| 4,890,235 A * | 12/1989 | Reger et al. ................ 700/118 |
| 4,998,354 A * | 3/1991 | Silverman et al. ......... 33/514.2 |
| 5,060,174 A * | 10/1991 | Gross ......................... 702/139 |
| 5,170,364 A * | 12/1992 | Gross et al. ................ 702/139 |
| 5,253,656 A * | 10/1993 | Rincoe et al. ................ 73/172 |
| 5,357,804 A | 10/1994 | Wesemann et al. |
| 5,375,397 A * | 12/1994 | Ferrand et al. ................. 54/66 |
| 5,687,099 A | 11/1997 | Gross et al. |
| 5,821,415 A | 10/1998 | Faust et al. |
| 5,877,436 A | 3/1999 | Faust et al. |
| 6,009,750 A | 1/2000 | Maurer et al. |
| 6,045,180 A * | 4/2000 | Clutton ...................... 297/202 |

FOREIGN PATENT DOCUMENTS

| | | |
|---|---|---|
| DE | 32 27 550 A1 | 1/1983 |
| DE | 36 25 210 A1 | 2/1988 |
| DE | 36 34 855 C1 | 3/1988 |

(Continued)

*Primary Examiner*—Peter R. Brown
(74) *Attorney, Agent, or Firm*—McGlew and Tuttle P.C.

(57) ABSTRACT

A method and a device are provided for individually adapting the saddle of a two-wheeled vehicle, especially bicycle saddles. The local pressing pressure of the buttocks of a test subject is measured on a adapting device (1) with a measuring saddle (2) and a pressure-measuring device (4) arranged on or in the seat surface at individual points or over a large area and in a localizing manner and evaluated. The two-wheeled vehicle saddle (8) is specifically adapted to the shape of the individual buttocks corresponding to the measuring results and is additionally cushioned where the contact pressure is higher.

16 Claims, 4 Drawing Sheets

FOREIGN PATENT DOCUMENTS

| | | |
|---|---|---|
| DE | 41 31 257 C2 | 7/1993 |
| DE | 43 24 457 A1 | 1/1995 |
| DE | 43 27 234 A1 | 2/1995 |
| DE | 44 05 595 C2 | 6/1995 |
| DE | 195 32 227 A1 | 3/1997 |
| DE | 196 01 971 C2 | 7/1997 |
| DE | 196 01 974 C2 | 7/1997 |
| DE | 196 25 730 A1 | 1/1998 |
| DE | 197 20 854 C1 | 10/1998 |
| DE | 199 10 194 A1 | 10/2000 |
| DE | 696 10 407 | 2/2001 |
| EP | 0 327 824 A2 | 8/1989 |

* cited by examiner

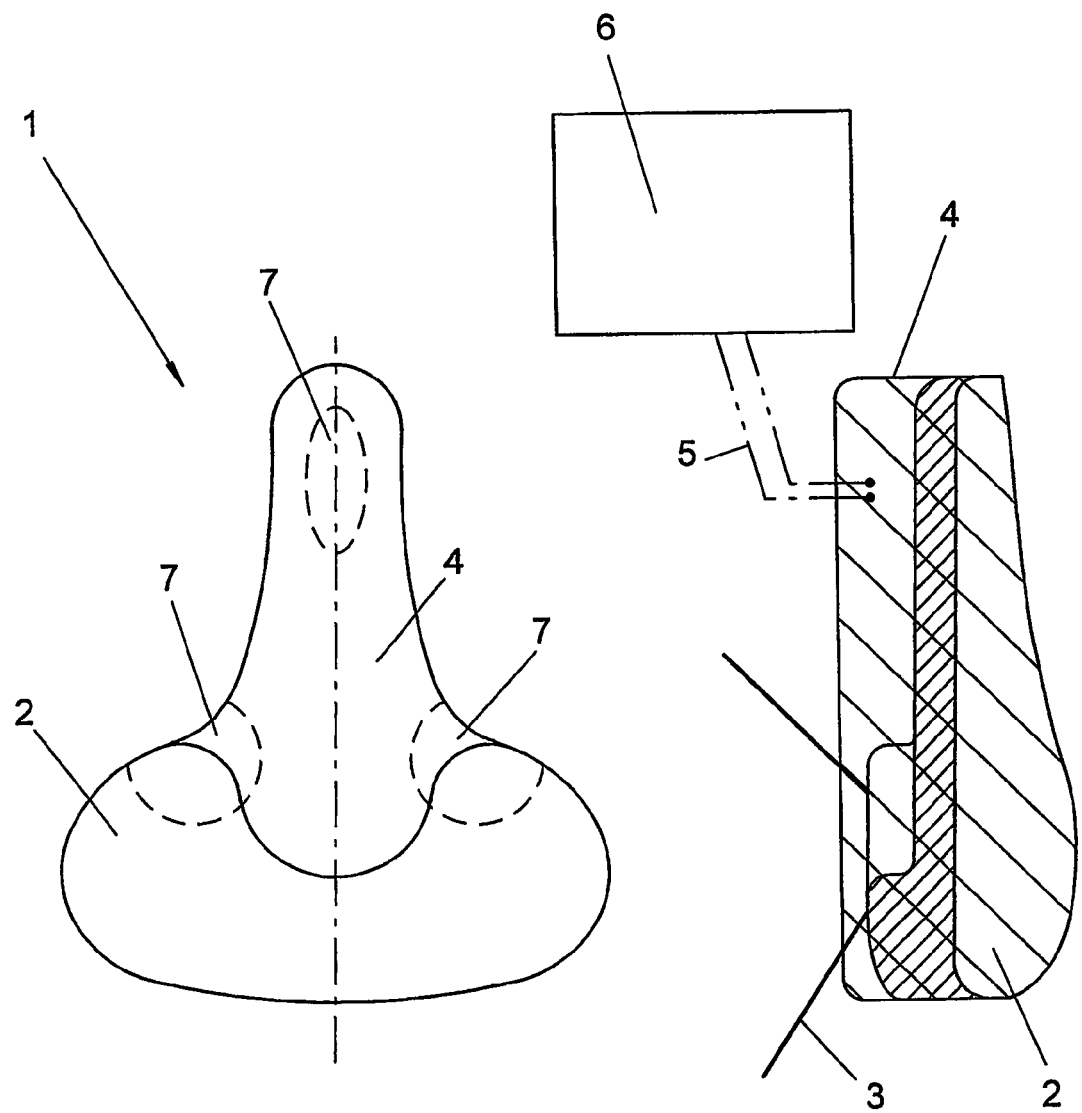

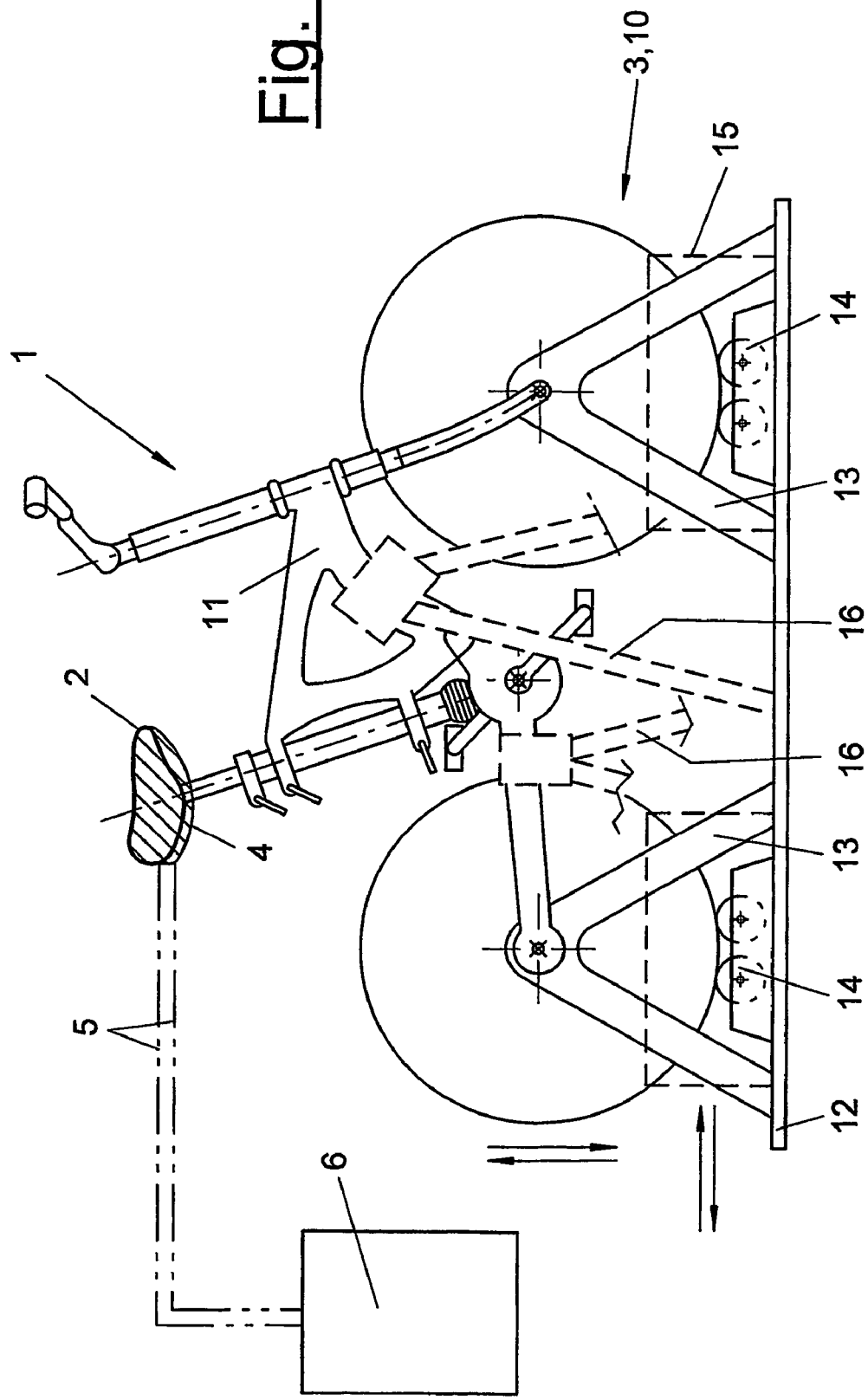

METHOD FOR INDIVIDUALLY ADAPTING THE SADDLE OF A TWO-WHEEL VEHICLE

FIELD OF THE INVENTION

The present invention pertains to a process for individually adapting two-wheeled vehicle saddles, especially bicycle saddles, and to an adapting device as well as to the two-wheeled vehicle saddles manufactured accordingly.

BACKGROUND OF THE INVENTION

It is known from DE-A 195 32 227 that a bicycle saddle can be individually adapted to the shape of the user's buttocks. This is done here by means of a saddle material that can change its shape, e.g., by means of a flexible saddle cover that can be filled with a material that can change its shape. The cover may be filled with air or a fine granular, flowable filling material. The cover itself consists of a flexible material.

A self-adapting bicycle saddle is known from DE-A 36 25 210. The saddle is filled here with a moldable mass, which is at first flexible and flowable and automatically adapts itself to the shape of the buttocks as a result. The material is said to subsequently solidify and retain its adapted shape as a result.

Another such individual bicycle saddle is known from DE-A 43 27 234. The saddle is said to use parts or inserts that are molded or foamed individually according to the anatomic conditions.

The problem of these prior-art adaptable saddles is that the filling material used is not well suited for the requirements imposed on a bicycle saddle during continuous operation. Thus, the prior-art adapted vehicle saddles cannot satisfy all demands.

A pressure-measuring device for seat shells or seat backs, in which an image of the body shape of a person can be determined with a pressure sensor each by means of mobile measuring strips and stored electronically, is known from DE-A 43 24 457. Based on the results of the measurements, a conventional seat or optionally also a wheelchair for elderly people can be correspondingly adapted. DE-A 41 31 257 shows a similar device, which operates with sensors in the form of capillary tubes.

A seat testing stamp and a process for the quantitative determination of the pressure comfort of a seat pad, with which standardized vehicle seats can be checked and classified with respect to their pressure comfort, are known from DE-A 196 01 971 and DE-A 196 01 974. The seat testing stamp represents here the standard shape of a human body. The purpose of this technique is to make it possible to manufacture vehicle seats that offer maximum comfort for as many different human body shapes as possible.

DE-A 41 31 257, DE-C 36 34 855 and DE-A 199 10 194 pertain to measuring set-ups for measuring forces or pressures. For example, it can be determined based on these measuring results whether a person is located on a vehicle seat and how much he weighs in order to make it possible subsequently to activate and especially trigger an air bag or another part of the vehicle correspondingly.

SUMMARY OF THE INVENTION

The object of the present invention is to provide a better possibility for the individual adaptation and manufacture of two-wheeled vehicle saddles.

According to the invention, a process is provided for individually adapting two-wheeled vehicle saddles, especially bicycle saddles. The process includes measuring a local pressing pressure of the buttocks of a test subject on an adapting device with a measuring saddle and a pressure-measuring means arranged on or in the seat surface at individual points or over a large area and in a localizing manner. The measurement is evaluated and the two-wheeled vehicle saddle is specifically adapted to the shape of the individual buttocks corresponding to the measuring results.

The adaptation process and the adapting device used therefor have the advantage that the local pressure conditions can be measured and localized at least in the critical area of the seat surface. The measurement is preferably performed on the entire surface of the seat.

The three contact areas at the pubic bone and at the two lateral tuberosities of the ischium are especially relevant on the buttocks. The local positions and the pressure conditions of these three points of the buttocks may vary individually and, moreover, depend on the sitting position. These individual peculiarities can be taken into account optimally with the adaptation process and the adapting device.

A corresponding measuring saddle with a pressure-measuring device is used for the adaptation. Based on these localized pressure conditions, the two-wheeled vehicle saddle can then be manufactured individually to size and adapted to the actual shape of the buttocks. For example, special padding can be performed for this in the problem zones and/or an adapted shaping can be performed.

A suitable pressure-measuring means is especially a flexible pressure-measuring film, which optimally adapts itself to the shape of the saddle and furnishes accurate measuring results. The value and the position of the local pressure on the buttocks can be exactly determined. The resolution of the measuring results is very fine and accurate.

A plurality of standardized measuring saddles of different sizes and shapes may be used to take into account different body sizes and other individualizing standards. It is also possible, e.g., to make distinctions for this according to the intended purpose, e.g., according to touring bike saddles, racing bike saddles or the like.

To make possible measurements that can be carried out under practical conditions, the adapting device has a suitable frame for the measuring saddle. This frame has a design similar to that of the particular two-wheeled vehicle in question and makes it possible to assume a practical sitting position during the measurement. The frame may also be adjustable for this purpose in order to respond to different bicycle sizes, bicycle models, types of seats, etc.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 2 is an enlarged top view of the measuring saddle;

FIG. 3 is a partially sectional tilted side view of the measuring saddle with the pressure-measuring means and an evaluating means;

FIG. 6 is a side view of an adapting device with a frame designed as a bracket for two-wheeled vehicles.

DESCRIPTION OF THE PREFERRED EMBODIMENTS

Figure 1:
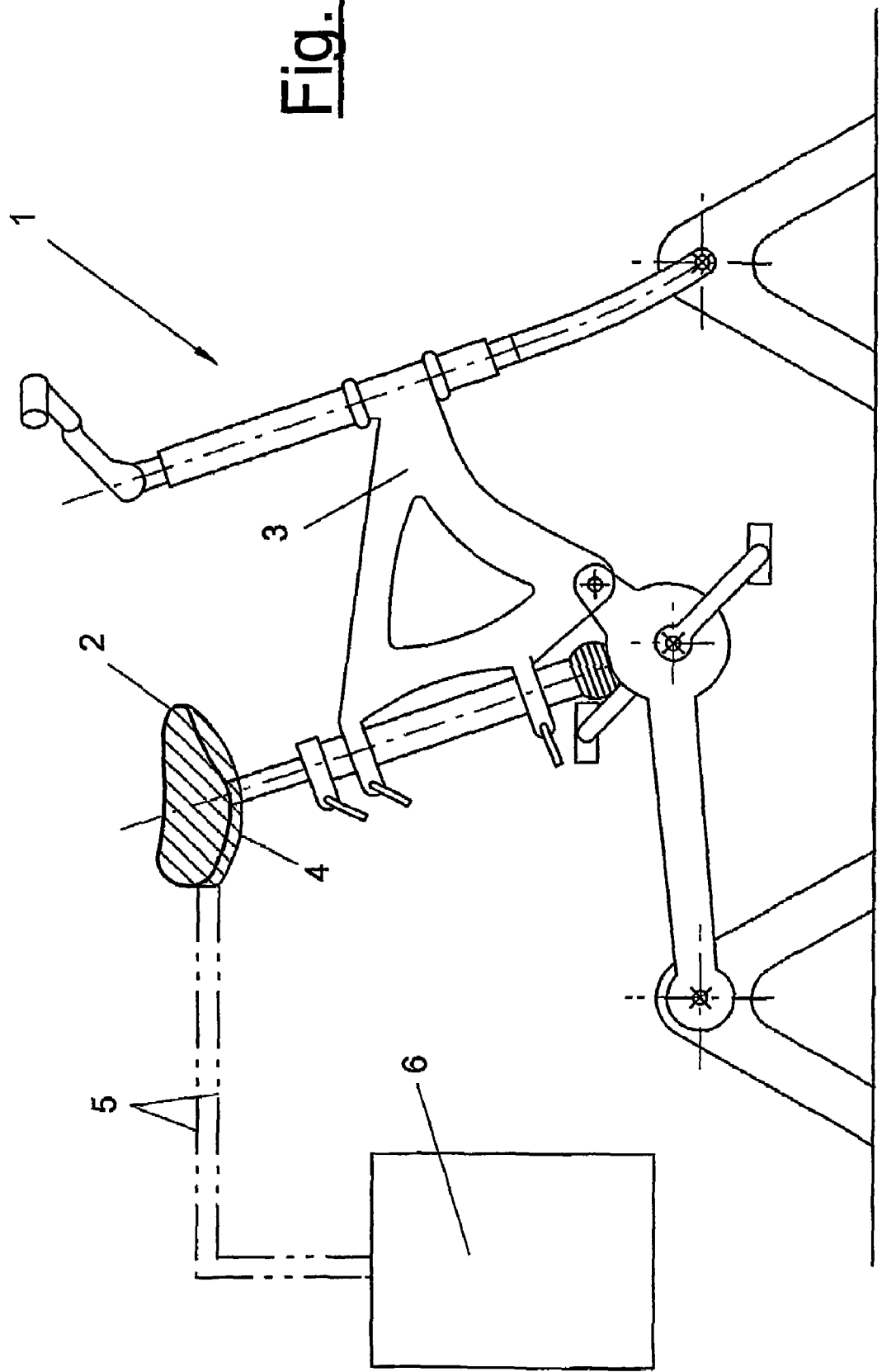
FIG. 1 is a schematic side view of an adapting device with a measuring saddle and a pressure-measuring means.

Referring to the drawings in particular, FIGS. 1 through 3 and 6 show an adapting device 1, which makes it possible to manufacture two-wheeled vehicle saddles 8, preferably bicycle saddles, individually to size. As an alternative, it may also be another saddle, especially a two-wheeled vehicle saddle 8, e.g., a motorcycle saddle, etc. Such two-wheeled vehicle saddles 8 have a banana-like or bench-like shape, which is surrounded by the legs of the person sitting astride at least in some areas at the top and laterally.

The adapting device 1 comprises one or more standardized measuring saddles 2, which embody a basic saddle shape and/or a basic saddle size. A plurality of different measuring saddles 2 may be used, which may differ from each other partly in size, by making a distinction between, e.g., saddles for children, ladies and men. In addition, the measuring saddles 2 may have different shapes, which are adapted to the particular intended purpose or bicycle model, e.g., mountain bikes, touring bikes, racing bikes, etc., to different demands on comfort or the like. The saddle may be, e.g., a more comfortable and soft touring bike saddle suitable for comfortable sitting for a long time, a harder and slimmer, banana-shaped racing bike saddle or the like.

To make measurements possible under practical conditions, the adapting device 1 has a suitable frame 3 for the detachable, replaceable and variable arrangement of the measuring saddle 2. This frame 3 may have any suitable shape. It is preferably designed similarly to a two-wheeled vehicle with frame, handlebar as well as pedals and is stationarily supported on the floor by means of bearing blocks instead of the wheels. As a result, it enables the test subject not shown to assume a practical sitting position during the measurement. The frame and its parts may likewise be adjustable in size, orientation and/or shape in order to make it possible to simulate different bicycle sizes, bicycle models, handlebar positions, seat heights, seat types, etc. Individual parts, e.g., the handlebar, can also be replaced.

Due to the possibilities of adjusting the adapting device 1 in a highly flexible manner, personal peculiarities of the test subject, e.g., individual sitting and riding positions, possible mispositions of the body, anomalies, physical disabilities and the like can be optimally taken into account and they can specifically affect the adaptation of the saddle. Likewise, the test subject's own bicycle model can be simulated and taken into account during the adaptation.

The measuring saddles 2 preferably have little padding or no padding at all. The padding may have uniform size everywhere. However, a somewhat thicker padding may also be present from the outset in known problem zones as an alternative.

The adapting device 1 comprises, furthermore, a pressure-measuring means 4 for the preferably two-dimensional and localizing measurement of the local pressing pressure of the buttocks of a test subject. The pressure-measuring means 4 is arranged at least on or in the seat surface of the measuring saddle 2. As a result, it is possible to measure the local pressing pressure of the buttocks at a plurality of points distributed on the seat surface of the measuring saddle 2 as uniformly as possible to localize this measured value. It is possible, in particular, to detect and specifically measure the pressure conditions at the pubic bone and the two ischial tuberosities.

It can be determined in this way where one or more problem zones 7 exist, at which the test subject's buttocks are in contact with the seat surface of the measuring saddle 2 with a different, especially higher pressure than in other areas. Such problem zones 7 are schematically shown, e.g., in FIG. 2 on a usual touring bicycle saddle, which has a central front saddle tip and a broadened rear part adjoining it in the rear. The pubic bone is in contact, e.g., in the area of the tip of the saddle, while the two lateral ischial tuberosities are in contact with the broadening transition areas to the rear part. These problem zones 7 are individual and may occur in completely different areas and with different intensities and values. In addition, other zones with reduced pressing pressure can be detected and localized as well.

The pressure-measuring means 4 is designed as a highly flexible, especially flexurally elastic electric pressure distribution measuring film or mat, which preferably has a high tensile strength and is connected via lines 5 to a connected evaluating means 6. The evaluating means 6, equipped with a computer or another computing unit, generates a diagram or a graph, in which the local distribution of the pressure conditions on the seat surface of the measuring saddle 2 is shown. The diagram or the graph may be displayed on a connected monitor as a 2D or optionally also 3D graphic. In addition, it may be temporarily or permanently outputted on any other suitable output unit, e.g., a printer, plotter or the like.

The pressure-measuring means 4 may be designed, e.g., according to DE-A 32 27 550, DE-C 36 34 855, DE-A 199 10 194 or EP-A 0 327 824 and have a plurality of capacitive electronic pressure-measuring sensors distributed uniformly in a matrix. As an alternative, the pressure-measuring means 4 may also have any other suitable design and have, e.g., a plurality of fluidic sensors according to DE 41 31 257.

The pressure distribution-measuring film 4 may be permanently fastened to the measuring saddle 2. However, as an alternative, it may also be held loosely or replaceably, e.g., in the form of an elastic saddle cover, which is cut in such a way that it is at least approximately adapted to the shape of the saddle and tightly clings to the measuring saddle 2 due to its elasticity. The pressure distribution-measuring film 4 may be fixed on the measuring saddle 2 due to its own elasticity, by a tensioning rubber or the like. Moreover, it is recommended that a defined and reproducible spatial assignment be created between measurement points and the saddle by means of localizing pins, fixing dogs or fixing folds or other suitable fitting means for the defined localization of the results of the pressure measurement.

To localize the problem zones 7 and the compensatory measures necessary for them, especially paddings 9 on the measuring saddle 2, it is possible, e.g., for the evaluating means 6 to furnish a calculated graphic expression of the pressure distribution on the monitor or printer, where a 2D view or a printout represents the flat elevation or the developed view of the spatial distribution of the points. Using suitable fitting marks, the printout can be placed on the saddle 2 in an accurately fitting manner in order to make it possible to mark here the local areas of the necessary paddings 9 or the like. A two-wheeled vehicle saddle 8 corresponding to the measuring saddle 2 or the measuring saddle 2 itself can then be processed for adaptation to the buttocks corresponding to these markings.

In a variation, it is possible, e.g., to represent the location and the form of the problem zones 7 in a spatial 3D view on a monitor, e.g., as a transparent wire model. The view is optically detected by a saddle-maker or another saddle-processing worker and transferred to the two-wheeled vehicle saddle 8 to be processed by optical comparison, and marked. The individual adaptation of the saddle can then be performed on the basis of the markings.

As an alternative, the pressure-measuring film may also be integrated within the measuring saddle 2, in which it forms the outer skin or cover of the measuring saddle 2. In another variant, the pressure-measuring means 4 may also comprise a plurality of individual pressure-measuring sensors, which are permanently or temporarily positioned at defined sites and are all connected to an evaluating means 6 via lines.

The measuring saddle 2 may be a kind of measuring gauge, which can be used in a simple manner and on which the pressure-measuring sensors are arranged in a suitable manner, preferably permanently. The shape of the measuring saddle 2 corresponds in this case to the basic shape of a two-wheeled vehicle saddle 8 to be adapted, to which the position of the measured problem zones 7 is transferred in a suitable manner. There are correspondingly different gauges or measuring saddles 2 for different two-wheeled vehicle saddles 8. The measuring saddle or measuring saddles 2 is/are part of the adapting device 1 in this case.

As an alternative, the two-wheeled vehicle saddle 8 to be adapted may itself represent the measuring saddle 2, and the pressure-measuring film 4 or another suitable sensor system is temporarily arranged at the saddle for the pressure measurement. The measured problem zones 7 can be marked directly at the saddle 8 in a suitable manner, and the two-wheeled vehicle saddle 8 is subsequently processed and individually adapted after removal of the pressure-measuring film 4. The pressure-measuring film 4 or the like is fastened detachably in this case and can be used several times. A flexible pressure-measuring film 4 can also now be used for different types and sizes of two-wheeled vehicle saddles 8. The design effort and the cost of the adapting device 1 may be lower in such a case than in the case of gauge type measuring saddles. In addition, the range of variation and the available number of adaptable saddles are greater. The two-wheeled vehicle saddle 8 is part of the adapting device 1 only temporarily in this variant, and the adapting device I comprises essentially only the pressure-measuring means 4 and the evaluating means 6 as well as optionally the frame 3.

Figure 4:
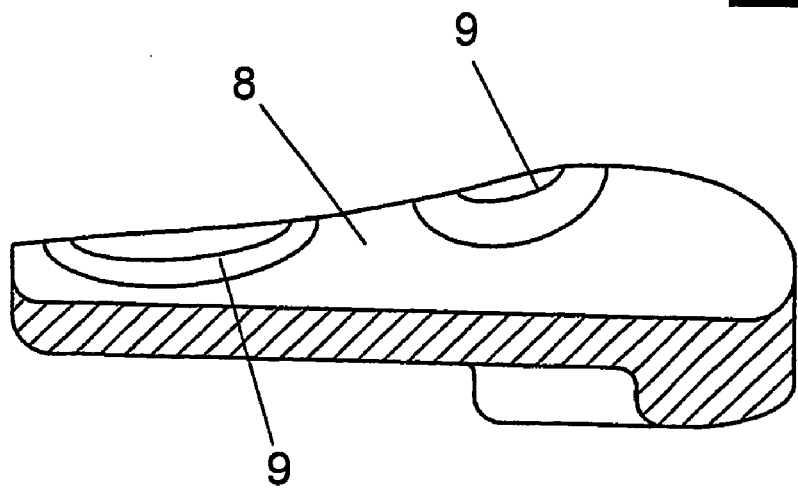
FIG. 4 is a side view of an adapted two-wheeled vehicle saddle.
Figure 5:
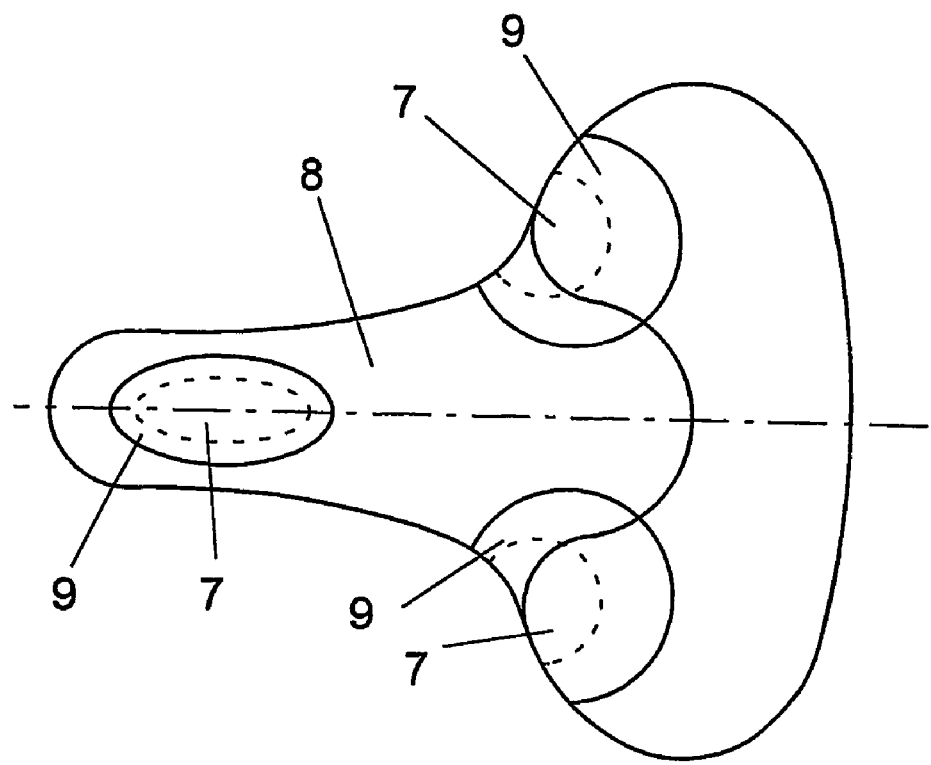
FIG. 5 is a top view of the adapted two-wheeled vehicle saddle shown in FIG. 4.

FIGS. 4 and 5 illustrate the two-wheeled vehicle saddle 8 made ultimately to size, here a bicycle saddle. Corresponding to the measuring results, this saddle is provided with an adapted, optionally additional and especially softer padding 9 on the identified problem zones 7 with increased pressing pressure and optionally also in the surrounding, adjacent area. The other area[s] of the saddle are harder or are not padded at all. As a result, they can ensure the good guiding and force transmission between the buttocks and the two-wheeled vehicle. The two-wheeled vehicle saddle 8 optionally comprises a saddle frame with a thin saddle shell, which may be relatively hard and only slightly flexible, e.g., in the case of racing bike saddles. This shell is then padded in the problem zones 7 only and is relatively hard in the other area[s], which may be advantageous for the guiding of the buttocks. By contrast, touring bike or comfort saddles may also have a padding outside the problem zones 7, but this padding is harder, or these saddles may also have increased flexibility.

As an alternative or in addition, the shaping of the two-wheeled vehicle saddle 8 may be changed and especially reduced. The saddle contour is changed by corresponding indentations or depressions in the problem zones 7 with increased pressing pressure, and the pressing pressure is made uniform as a result.

The shaping can likewise be changed and especially widened by means of bulges or the like at sites or zones with reduced pressing pressure. As an alternative or in addition, the two-wheeled vehicle saddle 8 may be hardened or made stiffer in these areas by eliminating the padding by removing soft zones.

As a result, the two-wheeled vehicle saddle can also be manufactured as a whole in a highly individual manner and to size by being exactly adapted at all sites of the seat surface to the pressure conditions of the individual buttocks, which pressure conditions were determined with the adapting device 1, and thus it has an adapted padding and/or shape at all points of the seat surfaces. Due to the fact that the pressing pressure of the buttocks is made uniform on the individually adapted two-wheeled vehicle saddle 8, optimized adaptation of the shape to the particular shape of the buttocks can also be performed at the same time.

In another embodiment, not shown, it is possible to work with a completely different pressure-measuring means 4, especially if the two-wheeled vehicle saddle 8 is used as a temporary measuring saddle 2. The pressure-measuring means 4 may consist in this case of a web, film or another similar measuring layer, which can be placed temporarily over the two-wheeled vehicle saddle 8 in such a way that it closely adapts the shape of the said saddle 8. The pressure-measuring means 4 now comprises measuring elements which change their appearance, e.g., their color, under pressure and based on this change they locally signal the problem zones 7 with increased pressing pressure directly at the measuring saddle 2. Pressure-sensitive silicone layers, but also pressure-sensitive gel layers or the like may be used as measuring elements. A change in brightness, a change in the surface or other suitable indications or signals that respond to pressure may also be used instead of a change in color. The problem zones 7 can be marked in this variant on the two-wheeled vehicle saddle 8 in a suitable manner during the indication, which may be temporary, e.g., by perforations prepared with needles, color markings or the like.

In a variant shown in FIG. 6, the frame 3 may be a preferably adjustable bracket 10, in which the own two-wheeled vehicle 11, especially bicycle, can be received and fixed, together with the test subject sitting on it for performing the pressure measurement. An especially individual pressure measurement and saddle adaptation, which are based exactly on the test subject's own equipment, can be achieved as a result. The design effort and the engineering effort for the bracket 10 or the frame 3 is, moreover, very low, and it nevertheless makes it possible to completely cover all models of two-wheeled vehicles. The measuring saddle 2 is preferably the test subject's own two-wheeled vehicle saddle 8 in this case.

The bracket 10 may comprise, e.g., a bottom part 12 and two support blocks 13 guided adjustably thereon for mounting the two-wheeled vehicle axles in a nondisplaceable and nontiltable manner. Furthermore, the tires may be supported on freely rotatable rollers 14 in order to simulate real riding situations.

As an alternative, the bracket 10 may have adjustable clamping rails 15 for guiding the wheels or tires and one or more support clamps 16 acting separably and adjustably on the frame of the two-wheeled vehicle. These parts are indicated by broken lines in FIG. 6.

Various other modifications of the invention described are possible. On the one hand, the features of the different embodiments may be combined and exchanged with each other as desired. Furthermore, the design embodiment of the frame 3, the measuring and two-wheeled vehicle saddles 2, 8 and the pressure-measuring and evaluating means 6 may be varied as desired for achieving the same function according to the present invention.

While specific embodiments of the invention have been shown and described in detail to illustrate the application of the principles of the invention, it will be understood that the invention may be embodied otherwise without departing from such principles.

The invention claimed is:

1. A process for individually adapting two-wheeled vehicle saddles, the process comprising:
   measuring the local pressing pressure of the buttocks of a test subject on an adapting device with a measuring saddle having a seat surface, and a pressure-measuring device arranged on or in said seat surface with plural individual measuring points or over a large area and in a localizing manner;
   evaluating the measurement results;
   producing a two-wheeled vehicle saddle based on said measurement results such that said two-wheeled vehicle saddle is formed specifically to the shape of the buttocks of the test subject.

2. A process in accordance with claim 1, wherein the two-wheeled vehicle saddle is additionally padded and/or its shape is reduced at points with increased pressing pressure.

3. A process in accordance with claim 1, wherein the padding is eliminated in the two-wheeled vehicle saddle and the shape of the two-wheeled vehicle saddle is widened at points with reduced pressing pressure.

4. A process in accordance with claim 1, wherein the two-wheeled vehicle saddle is temporarily provided with the pressure-measuring device detachably arranged and used as the measuring saddle.

5. A process m accordance with claim 1, wherein said measuring saddle comprises a central front saddle tip and a broadened rear part having a left side portion and a right side portion, said broadened rear part adjoining said saddle tip, said front saddle tip having a first side leg extending surface and a second leg extending surface, one measuring point being located in said central front saddle tip, another measuring point being located on said right side portion, another measuring point being located on said left side portion.

6. A process in accordance with claim 5, wherein said evaluating step includes evaluating the pressure at said central front saddle tip, said left side portion of said broadened rear part and said right side portion of said broadened rear part.

7. A process in accordance with claim 5, wherein said measuring step includes measuring the pressure at said central front saddle tip, said left side portion and said right side portion.

8. An adapting device for the individual manufacture of two-wheeled vehicle saddles, the adapting device comprising:
   an elastic pressure-measuring means for two-dimensional and localizing measurement of the local pressuring pressure of the buttocks of a test subject;
   a measuring saddle having a seat surface, said pressure-measuring means being arranged on or in the seat surface at a plurality of measuring points such that said elastic pressure-measuring means conforms to the shape of said measuring saddle, said measuring saddle comprising a central front saddle tip and a broadened rear part having a left side portion and a right side portion, said broadened rear part adjoining said saddle tip, said front saddle tip having a first side leg extending surface and a second leg extending surface, each measuring point being located at said central front saddle tip, said right side portion and said left side portion.

9. An adapting device in accordance with claim 8, wherein the pressure-measuring means comprises a flexible pressure-measuring film.

10. An adapting device in accordance with claim 8, wherein the pressure-measuring means can be detachably connected to the measuring saddle or the two-wheeled vehicle saddle to be adapted.

11. An adapting device in accordance with claim 8, wherein the pressure-measuring means can be connected to a evaluating means via lines.

12. An adapting device in accordance with claim 8, wherein the adapting device has a plurality of standardized measuring saddles of different shapes and/or sizes.

13. An adapting device in accordance with claim 8, wherein the measuring saddle has a frame similar to that of a two-wheeled vehicle.

14. An adapting device in accordance with claim 13, wherein the frame is adjustable.

15. An adapting device in accordance with claim 13, wherein the frame is designed as a bracket for two-wheeled vehicles.

16. An individually adapted two-wheeled bicycle saddle or two wheeled vehicle saddle, the saddle comprising:
   a saddle base structure comprising a central front saddle tip and a broadened rear part having a left side portion and a right side portion, said central front saddle tip having a first leg extending surface for contact with one leg of a test subject and a second leg extending surface for contact with another leg of the test subject; and
   padding and/or padding structure, said padding being positioned in said central front saddle tip based on local pressing pressure measurement at said central front saddle tip via an adapting device, said padding being located at said left side portion based on local pressing pressure measurement at said left side portion via the adapting device, said padding being positioned at said right side portion based on the local pressing pressure measurement at said right side portion.

* * * * *